United States Patent [19]

Peake

[11] 4,390,707
[45] Jun. 28, 1983

[54] BIS-THIOALKYLFURANS USEFUL AS CYCLOPENTENONE PROSTAGLANDIN INTERMEDIATES

[75] Inventor: Steven L. Peake, New Canaan, Conn.

[73] Assignee: American Cyanamid Company, Stamford, Conn.

[21] Appl. No.: 344,980

[22] Filed: Feb. 2, 1982

[51] Int. Cl.³ .................. C07D 309/06; C07D 307/40
[52] U.S. Cl. .................................... 549/214; 549/502; 549/483; 549/453; 549/449; 549/414; 549/21; 568/361; 568/379
[58] Field of Search .................. 549/414, 502, 21, 214

[56] References Cited

U.S. PATENT DOCUMENTS 4,254,285 11/1980 Wissner .............................. 568/379

OTHER PUBLICATIONS

B. T. Grobel and D. Seebach, Synthesis, 6, 357 (1977).

*Primary Examiner*—Nicky Chan
*Attorney, Agent, or Firm*—Robert P. Raymond; Richard J. Hammond

[57] ABSTRACT

A method for the preparation of cyclopentenones of the general formula (VIII):

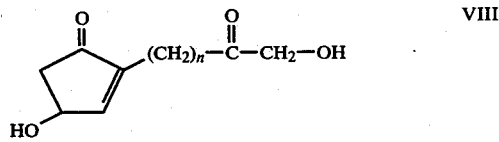

wherein n is 5-7, has been developed which proceeds via the acid catalyzed deprotection and rearrangement of novel substituted-α-hydroxymethylfurans of general formula (VII):

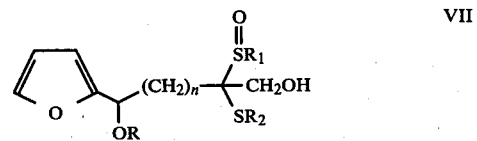

wherein R is a hydroxyl protecting group, $R_1$ and $R_2$ are methyl or ethyl or together form $-(CH_2)_3-$ and n is as above described. Cyclopentenones of formula VIII are useful intermediates in prostaglandin analog synthesis.

10 Claims, No Drawings

BIS-THIOALKYLFURANS USEFUL AS CYCLOPENTENONE PROSTAGLANDIN INTERMEDIATES

BACKGROUND OF THE INVENTION

The synthesis of cyclopentenones of type VIII

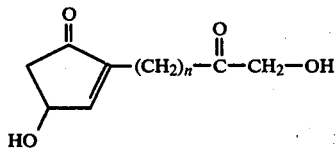

wherein n is 5–7, preferably 6, and their use as key intermediates in the synthesis of prostaglandin analogs of pharmacological interest have been described in U.S. Pat. No. 4,254,285, which is incorporated herein by reference, as though fully set forth herein. The synthesis of cyclopentenones (VIII) as reported in U.S. Pat. No. 4,254,285, Flowsheet K involves the conversion of cyclopentenones of type IX

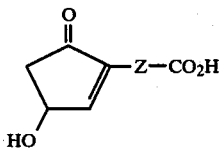

wherein Z is $-(CH_2)_g-$, wherein g is 5–7 to cyclopentenones of type VIII, wherein n is as above described. In the method of this patent conversion of the carboxylic acid moiety of IX into a hydroxymethylketo moiety employs either diazomethane or 1,1,2-tris-trimethylsiloxyethylene. (Dimethyl)-t-butylsilane is also employed.

In accordance with the method of the present invention cyclopentenones of type VIII are generated in one step by the acid-catalyzed deprotection and rearrangement of a protected α-hydroxymethylfuran which incorporates a protected hydroxymethylketo moiety.

BRIEF DESCRIPTION OF THE INVENTION

The subject matter of this invention includes a process for preparing a prostaglandin intermediate comprising the steps of reaching a bromoalkylfuran of the formula:

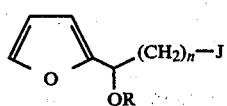

wherein n is 5–7, J is bromo or chloro, and R is a hydroxylprotecting group labile under neutral or acid conditions, with a bisthioanion of the formula:

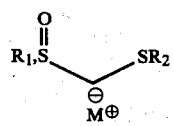

wherein $R_1$ and $R_2$ are lower alkyl groups such as methyl or ethyl or together form $-(CH_2)_3-$, and M is lithium, sodium or potassium, to provide a bisthioalkylfuran of the formula:

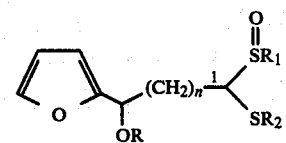

wherein R, $R_1$, $R_2$ and n are as above described; deprotonating the bisthioalkylfuran at $C_1$, and reaching the bisthioalkylfuran with gaseous formaldehyde to afford a compound of the formula:

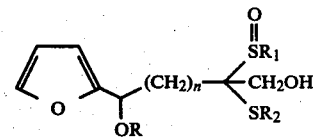

wherein R, $R_1$, $R_2$ and n are as above described.

This invention also comprises a process for the preparation of a cyclopentenone prostaglandin intermediate, comprising rearranging the compound of the formula:

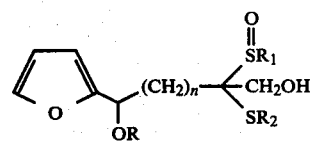

wherein $R_1$, $R_2$, n and R are as above described, to provide the cyclopentenone of the formula:

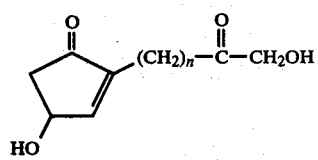

wherein n is as above described. Preferably this rearrangement is carried out by treating the furan intermediate with aqueous acid.

In addition, this invention provides the prostaglandin intermediate compounds of the formula:

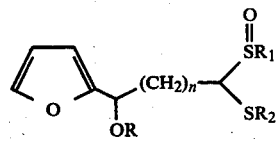

wherein $R_1$, $R_2$, n and R are as above described; as well as the compounds of the formula

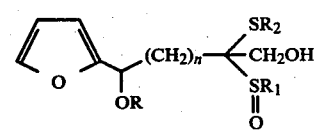

wherein $R_1$, $R_2$, R and n are as above described.

The subject matter of this invention will be described further with reference to the detailed description of the invention which follows.

DETAILED DESCRIPTION OF THE INVENTION

The method of the present invention is outlined in Flowchart I.

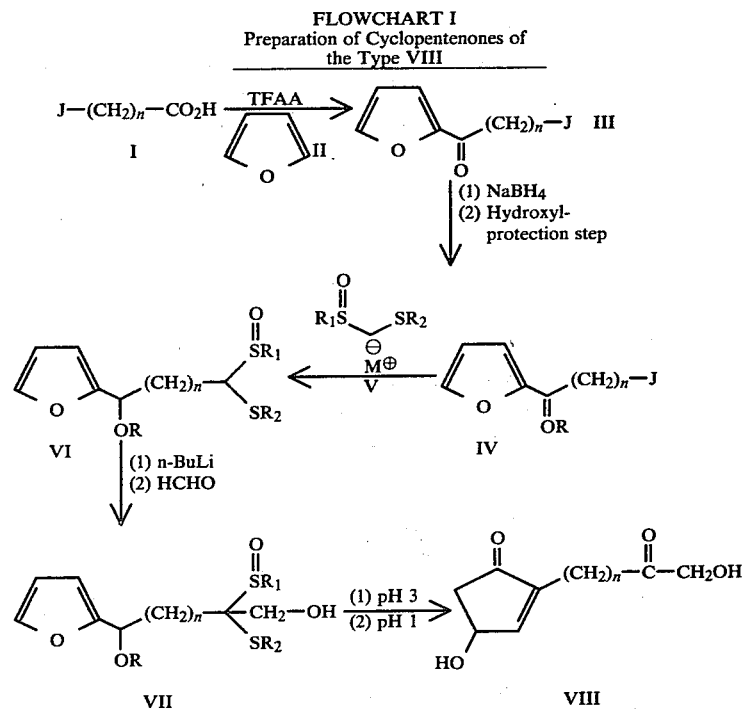

Furan (II) is acylated at about 25° C. with an ω-haloalkanoic acid of type I, wherein n is 5–7 and J is bromo or chloro, preferably bromo, in the presence of trifluoroacetic anhydride (TFAA) in a chlorinated solvent, preferably methylene chloride to afford ketofuran III, wherein n and J are as described above. This reaction scheme is described in U.S. Pat. No. 4,254,043, which is incorporated herein by reference.

Ketofuran III is reduced with a carbonyl reducing agent such as sodium or lithium borohydride in an alcoholic solvent such as ethanol at about −10° C.–25° C. for about 0.5–2.0 hours, and the resulting alcohol protected, for example, by the acid-catalyzed reaction with dihydropyran or 2-methoxypropene, or the base-catalyzed reaction with a tri-$C_1$-$C_4$-alkylsilyl chloride, to yield the haloalkylfuran IV, wherein R is a hydroxyl protecting group which is labile under neutral or acidic conditions, such as tetrahydropyran-2-yl, 2-methoxyprop-2-yl or tri-$C_1$-$C_4$-alkylsilyl and n and J are as described above. See. J. F. W. McOmie, "Protective Groups in Organic Chemistry," Plenum Press, New York 1973, p. 95f.

Haloalkylfuran IV, wherein R, J and n are as above-described, is reacted with a metallated, S,S-acetal-S-oxide of type V wherein $R_1$ and $R_2$ are lower alkyl groups and preferably methyl or ethyl, or together $R_1$ and $R_2$ are —$(CH_2)_3$—. M is lithium, sodium or potassium. Compounds IV and V are reacted at about −78° C. to −40° C. in an ethereal solvent, preferably dimethoxyethane to afford an alkylated furan of type VI wherein R, n, $R_1$ and $R_2$ are as above described after warming and stirring at 0° C. to 30° C. See B. T. Grobel and D. Seebach, Synthesis, 6, 357 (1977) which is incorporated by reference herein. This reference descibes the preparation of bisthioanions of Type V. A preferred metallated S,S-acetal-S-oxide of Type V is the lithio anion of methyl methylsulfinyl methyl sulfide.

Deprotonation of VI in dimethoxyethane at about −78° C. to −40° C. with an alkyllithium reagent, preferably n-butyllithium followed by reaction of the resultant bis-thioanion with gaseous formaldehyde (HCHO) at about −10° C. to +10° C. affords the hydroxymethyl-substituted furan VII, wherein $R_1$, $R_2$, R and n are as above described. It is preferred to carry out the second deprotonation and reaction with gaseous formaldehyde in the same reaction vessel, without the isolation of VI.

Rearrangement of hydroxymethylfuran VII, wherein R, $R_1$, $R_2$ and n are as above described may be carried out in dimethoxyethane and water at reflux temperatures under acidic conditions. Preferably the pH of the reaction mixture is first adjusted to about pH 3 with 85% phosphoric acid and refluxing continued for about 24 hours. After cooling to 50° C., the pH is adjusted to about 1.0 or less using concentrated sulfuric acid and refluxing continued up to an additional 24 hours to afford 2-cyclopenten-1-ones of type VIII wherein n is as above described.

Cyclopentenones of type VIII can be protected by the acid-catalyzed reaction with 2,2-dimethoxypropane or 3,3-dimethoxypentane by the methods described in U.S. Pat. No. 4,254,285, which is incorporated herein by reference, to afford compounds of formula IX:

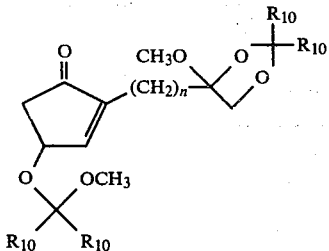

wherein n is as above described and $R_{10}$ is methyl or ethyl. Compounds of formula X may be employed in the conjugate addition reactions with activated prostaglandin β-chain reagents, to afford, after deprotection, a wide variety of prostaglandin analogs. See, Mitra, "The Synthesis of Prostaglandins," Wiley, N.Y., 1977. The reaction of compound IX with two such reagents is outlined in Flowchart II.

FLOWCHART II
Conjugate Addition Reaction

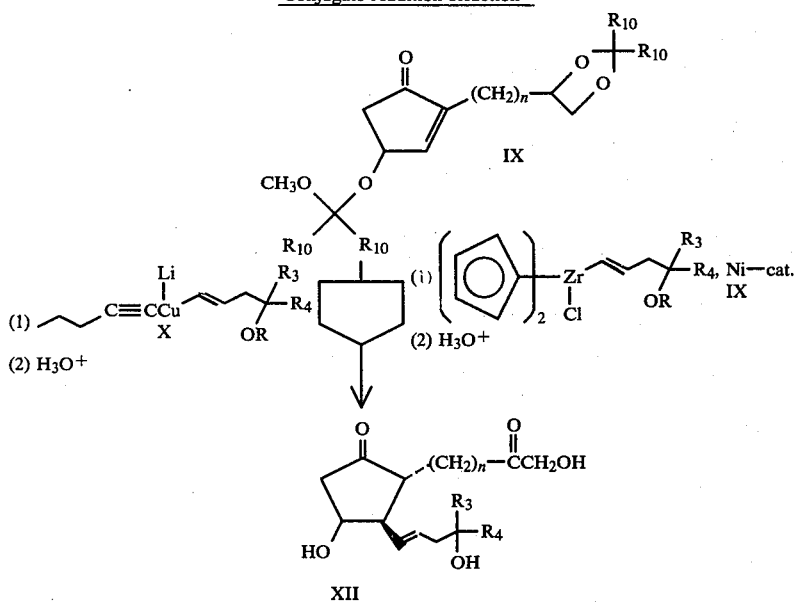

For example, the reaction of protected cyclopentenones of type IX, wherein n and $R_{10}$ are as above described, with activated prostaglandin β-chain reagents such as the lithiocuprate reagents of formula X wherein $R_3$ is vinyl or methyl, $R_4$ is a $C_4$-alkyl group, and R is as above described is disclosed in U.S. Pat. No. 4,254,285, which is incorporated herein by reference. The reaction of protected cyclopentenones of type IX, wherein n and $R_{10}$ are as above described with alkenylzirconium reagents of formula XI wherein $R_3$, $R_4$ and R are as above described is disclosed in U.S. Application Ser. No. 331,373, filed Dec. 16, 1981, which is incorporated herein by reference. After removal of the protecting groups with dilute aqueous acid, prostaglandin analogs of formula XII are obtained wherein $R_3$, n and $R_4$ are as above described.

The invention will be described with reference to the following detailed examples.

In the following examples tetrahydrofuran (THF) was freshly distilled from sodium benzophenone ketyl. Dimethoxyethane (DME) was dried over 40 angstrom molecular sieves. Reactions employing n-butyllithium were conducted under argon oven-dried syringes, needles and glassware.

EXAMPLE 1

Preparation of 6-(2-Furoyl)-1-bromohexane, (III, n=6).

A solution of 135 mmol of trifluoroacetic anhydride in 50 ml of dry methylene chloride was added to a stirred solution of 130 mmol of 7-bromoheptanoic acid in 200 ml of dry methylene chloride. After 15 minutes, a solution of 390 mmol of furan in 25 ml of dry methylene chloride was added in a steady stream to the reaction mixture, and the resultant mixture stirred at 25° C. for 2.0 hrs. The methylene chloride and trifluoroacetic acid were removed by evaporation in vacuo. The residue was dissolved in ether, washed with water and distilled in vacuo to afford the title compound, bp 114° (0.01 mm Hg), 89.7% yield.

EXAMPLE 2

Preparation of 5-(2-Furoyl)-1-bromopentane (III, n=5).

Following the procedure of Example 1, but substituting 6-bromohexanoic acid for 7-bromoheptanoic acid afforded the title compound in 93% yield.

EXAMPLE 3

Preparation of 7-(2-Furoyl)-1-bromoheptane, (III, n=7). Following the procedure of Example 1, but substituting 8-bromooctanoic acid for 7-bromoheptanoic acid affords the title compound.

EXAMPLE 4

Preparation of 7-(2-Furyl)-7-(tetrahydropyran-2-yloxy)-1-bromoheptane (IV, n=6, R=tetrahydropyran-2-yl).

Solid sodium borohydride was added to a solution of 6-(2-Furoyl)-1-bromohexane in 100 ml of absolute ethanol at 25° C. After 2.0 hr, the ethanol was evaporated in vacuo and the residue dissolved in ethyl ether. The ether solution was washed with saturated aqueous sodium chloride and dried over magnesium sulfate. Evaporation of solvents in vacuo afforded 15.3 g of crude alcohol (97% yield) to which was added 100 ml of methylene chloride, 4.0 mg of para-toluene sulfonic acid and 15.0 ml of dihydropyran. The reaction mixture was stirred at 25° C. for 1.0 hr, then washed with 10% aqueous sodium carbonate ($Na_2CO_3$), brine, and dried over anhydrous sodium sulfate ($Na_2SO_4$). The solvents were removed in vacuo and the crude product chromatographed on silica gel (10% ethyl acetate-hexane eluate) to afford 20.0 g of the title compound. $^1$H NMR (CDCl$_3$); δ7.23 (m, 1H), 6.13 (m, 2H), 4.52 (m, 2H), 3.52 (m, 2H), 3.26 (t, J=7.0 Hz, 2H), 1.4 (m, 16H).

EXAMPLE 5

Preparation of 7-(2-Furyl)-7-(2-methoxyprop-2-yloxy)-1-bromoheptane (IV, n=6, R=2-methoxyprop-2-yl).

Using the procedure of Example 4 above, 30.0 g of ketofuran (III, n=6), 2.2 g of sodium borohydride and 20.0 ml of 2-methoxypropene afforded 29.6 g of crude product which was bulb-to-bulb distilled to afford 11.6 g of the title compound. $^1$H NMR: δ7.31 (m, 1H), 6.24 (m, 2H), 4.10 (t, J=6.0 Hz, 1H), 3.37 (t, J=7 Hz, 2H), 2.23 (s, 3H), 1.80, 1.36 (m, 16H).

EXAMPLE 6

Preparation of 7-(2-Furyl)-7-trimethylsiloxy-1-bromoheptane (IV, n=6, R=trimethylsilyl).

The crude alcohol (26.0 g) obtained by the procedure of Example 4 was dissolved in 100 ml of methylene chloride and treated with 21.0 ml of triethylamine and 2.0 mg of imidazole. A solution of trimethylsilyl chloride (21 ml) in 25.0 ml of methylene chloride was added dropwise over 15 min. After stirring for 1.0 hr at 25° C., 50 ml of 10% aqueous sodium bicarbonate ($NaHCO_3$) was added. The organic phase was isolated, dried, and solvents evaporated in vacuo. Bulb-to-bulb distillation (125° C. at 1.0 mm) afforded 25.7 g of the title compound (77% yield). $^1$H NMR (CDCl$_3$): δ7.32 (m, 1H), 6.29 (m, 2H), 4.70 (t, J=6.5 Hz, 1H), 3.40 (t, J=6.5 Hz, 2H), 1.90, 1.43 (m, 10H), 0.18 (s, 9H).

EXAMPLES 7–12

Following the procedures of Examples 4, 5 or 6, the Furoylbromoalkanes of the table are reduced and protected to afford the corresponding protected-hydroxy-furyl-bromoalkanes of the table.

TABLE I

| | Protected-Hydroxy-Furyl-Bromoalkanes. | | |
|---|---|---|---|
| Example | Furoylbromoalkane of Example | Procedure of Example | Protected-Hydroxy-Furyl-Bromoalkane |
| 7 | 2 | 4 | 6-(2-Furyl)-6-(tetrahydropyran-2-yloxy)-1-bromohexane |
| 8 | 2 | 5 | 6-(2-Furyl)-6-(2-methoxyprop-2-yloxy)-1-bromohexane |
| 9 | 2 | 6 | 6-(2-Furyl)-6-trimethylsiloxy-1-bromohexane |
| 10 | 3 | 4 | 8-(2-Furyl)-8-(tetrahydropyran-2-yloxy)-1-bromooctane |
| 11 | 3 | 5 | 8-(2-Furyl)-8-(2-methoxyprop-2-yloxy)-1-bromooctane |
| 12 | 3 | 6 | 8-(2-Furyl)-8-trimethylsiloxy-1-bromooctane |

TABLE I-continued

| | Protected-Hydroxy-Furyl-Bromoalkanes. | | |
|---|---|---|---|
| Example | Furoylbromoalkane of Example | Procedure of Example | Protected-Hydroxy-Furyl-Bromoalkane |

EXAMPLE 13

Preparation of 8-(2-Furyl)-8-(tetrahydropyran-2-yloxy)-1-methylsulfinyl-1-methylthiooctane, (VII, R=tetrahydropyran-2-yl, $R_1=R_2$=methyl, n=6).

A. 1.6 M solution of n-butyllithium in hexane (15.0 mmol) was added to a solution of 1.8 g of methyl methylsulfinyl methyl sulfide (Aldrich Chemical Co.) (14.5 mmol) in 15.0 ml of dry DME at −78° C. After 30 mins. a solution of 5.0 g 7-(2-Furyl)-7-(tetrahydropyran-2-yl)-1-bromoheptane in 5.0 ml of THF was added to the solution of lithioanion V, $R_1=R_2$=methyl, M=Li. The cooling bath was removed and the solution was allowed to stir at 25° C. for 1.0 hr. The reaction was quenched with 10 ml of saturated aqueous ammonium chloride. Most of the DME was removed by evaporation in vacuo, then methylene chloride was added and the organic phase isolated. The organic phase was washed with brine, dried (MgSO$_4$) and evaporated in vacuo. The residue was stirred for 1.0 hr. with petroleum ether. The petroleum ether was decanted and the residual solvent evaporated in vacuo to afford 4.6 g (84% yield) of the title compound as a brown oil.

EXAMPLE 14–21

Following the procedure of Example 13 the protected-hydroxy-furyl-bromoalkanes of Examples 5 and 6 and of Table 1 are converted into the protected-hydroxy-furyl-1-methylsulfinyl-1-methylthioalkanes of the table.

TABLE II

| | Protected-Hydroxy-Furyl-1-Methylsulfinyl-1-Methylthioalkanes | |
|---|---|---|
| Ex. | Protected-hydroxy-furyl-bromoalkane of Ex. | Protected-hydroxy-furyl-1-methylsulfinyl-1-methylthioalkane |
| 14 | 5 | 8-(2-Furyl)-8-(2-methoxyprop-2-yloxy)-1-methylsulfinyl-1-methylthiooctane |
| 15 | 6 | 8-(2-Furyl)-8-trimethylsiloxy-1-methylsulfinyl-1-methylthiooctane |
| 16 | 7 | 7-(2-Furyl)-7-(tetrahydropyran-2-yloxy)-1-methylsulfinyl-1-methylthioheptane |
| 17 | 8 | 7-(2-Furyl)-7-(2-methoxyprop-2-yloxy)-1-methylsulfinyl-1-methylthioheptane |
| 18 | 9 | 7-(2-Furyl)-7-trimethylsiloxy-1-methylsulfinyl-1-methylthioheptane |
| 19 | 10 | 9-(2-Furyl)-9-(tetrahydropyran-2-yloxy)-1-methylsulfinyl-1-methylthiononane |
| 20 | 11 | 9-(2-Furyl)-9-(2-methoxyprop-2-yloxy)-1-methylsulfinyl-1-methylthiononane |
| 21 | 12 | 9-(2-Furyl)-9-trimethylsioxy-1-methylsulfinyl-1-methylthiononane |

EXAMPLE 22

9-(2-Furyl)-9-(tetrahydropyran-2-yloxy)-2-methylsulfinyl-2-methylthiononan-1-ol (VII, n=6, $R_1=R_2=$methyl, R=tetrahydropyran-2-yl).

A 1.6 M solution of n-butyllithium in hexane (30 mmol) was added to a solution of 3.6 g of methyl methylsulfinyl methyl sulfide in 30 ml of dry DME at −78° C. After 30 min., a solution of 10.0 g of 7-(2-Furyl)-7-(tetrahydropyran-2-yl)-1-bromoheptane in 10 ml of dry THF was added and the reaction mixture stirred for 3.0 hr. at 0° C. The reaction mixture was again cooled to −78° C. and 30 mmol of 1.6 M n-butyllithium in hexane added. The −78° C. cooling bath was replaced by a 0° C. cooling bath and gaseous formaldehyde, prepared by pyrolyzing 60 mmol of paraformaldehyde, was bubbled into the reaction mixture. Stirring was continued for 30 min., then 25 ml of saturated aqueous ammonium chloride was added. Most of the DME was evaporated in vacuo and the residue was washed 4 times with 25 ml of methylene chloride. The solution was dried (MgSO$_4$) and solvents evaporated in vacuo to afford a crude product which was purified via silica gel chromatography (2.5% ethyl acetate in hexane eluate) to afford 6.5 g (58%) of the title compound as a brown oil.

EXAMPLES 23-30

Following the procedure of Example 22, the protected-hydroxy-furyl-bromoalkanes of Examples 5 and 6 and of Table I are converted into the protected-hydroxy-furyl-2-methylsulfinyl-2-methylthioalkanols of the table.

TABLE III
Protected-Hydroxy-Furyl-2-Methylsulfinyl-2-Methylthioalkanols

| Ex. | Protected-hydroxy-furyl-1-Bromoalkane of Ex. | Protected-Hydroxy-Furyl-2-Methylsulfinyl-2-Methylthioalkanol |
|---|---|---|
| 23 | 5 | 9-(2-Furyl)-9-(2-methoxyprop-2-yloxy)-2-methylsulfinyl-2-methylthiononan-1-ol |
| 24 | 6 | 9-(2-Furyl)-9-trimethylsiloxy-2-methylsulfinyl-2-methylthiononan-1-ol |
| 25 | 7 | 8-(2-Furyl)-8-(tetrahydropyran-2-yloxy)-2-methylsulfinyl-2-methylthiooctan-1-ol |
| 26 | 8 | 8-(2-Furyl)-8-(2-methoxyprop-2-yloxy)-2-methylsulfinyl-2-methylthiooctan-1-ol |
| 27 | 9 | 8-(2-Furyl)-8-trimethylsiloxy-2-methylsulfinyl-2-methylthiooctan-1-ol |
| 28 | 10 | 10-(2-Furyl)-10-(tetrahydropyran-2-yloxy)-2-methylsulfinyl-2-methylthiodecan-1-ol |
| 29 | 11 | 10-(2-Furyl)-10-(2-methoxyprop-2-yloxy)-2-methylsulfinyl-2-methylthiodecan-1-ol |
| 30 | 12 | 10-(2-Furyl)-10-trimethylsiloxy-2-methylsulfinyl-2-methylthiodecan-1-ol |

EXAMPLE 31

Preparation of 2-(8-hydroxy-7-keto)octyl-4-hydroxy-2-cyclopenten-1-one (VIII, n=6).

A solution of 1.0 g (2.4 mmol) of 9-(2-furyl)-9-(tetrahydropyran-2-yloxy)-2-methylsulfinyl-2-methylthiononan-1-ol (Ex. 22) in 10 ml of 3:2 DME-water adjusted to pH3 with 85% phosphoric acid was refluxed for 24 hr. After cooling to 50° C., the pH was adjusted to 1.0 using concentrated sulfuric acid and refluxing was continued for another 24 hrs. The DME was evaporated in vacuo and the residue washed with CH$_2$Cl$_2$. The solution was dried (MgSO$_4$) and the solvents evaporated in vacuo. Preparative thin-layer chromatography of the residue (Silica Gel, 3% ethanol in ethyl acetate) afforded 0.15 g of the title compound.

EXAMPLES 32-34

Following the procedure of Example 31, the protected-hydroxy-furyl-2-methylsulfinyl-2-methylthioalkanols of Table III are converted into the 2-cyclopenten-1-ones of the table.

TABLE IV
2-Cyclopenten-1-ones

| Ex. | Protected-Hydroxy-Furyl-2-Methylsulfinyl-2-Methylthioalkanol of Ex. | 2-Cyclopenten-1-one |
|---|---|---|
| 32 | 5 or 6 | 2-(8-hydroxy-7-ketooctyl)-4-hydroxy-2-cyclopenten-1-one (VIII, n = 6) |
| 33 | 7, 8 or 9 | 2-(7-hydroxy-6-keto)heptyl-4-hydroxy-2-cyclopenten-1-one (VIII, n = 5) |
| 34 | 10, 11 or 12 | 2-(9-hydroxy-8-keto)nonyl-4-hydroxy-2-cyclopenten-1-one (VIII, n = 7) |

This invention has been described in terms of specific embodiments set forth in detail herein, but it should be understood that these are by way of illustration only, and that the invention is not necessarily limited thereto. Modifications and variations will be apparent from the disclosure and may be resorted to without departing from the spirit of this invention, as those skilled in the art will understand. Accordingly, such variations and modifications of the disclosed invention are considered to be within the scope of the invention and the following claims.

What is claimed is:

1. A compound of the formula:

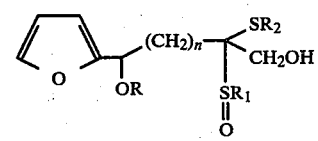

wherein R is a hydroxyl protecting group labile under neutral or acid conditions; $R_1$ and $R_2$ are both methyl or ethyl, or together are —(CH$_2$)$_3$—; and n is 5-7.

2. The compound according to claim 1 wherein both $R_1$ and $R_2$ are methyl groups.

3. The compound according to claim 1 wherein n is 6.

4. The compound according to claims 1 or 2 or 3 wherein R is a tri-C$_1$-C$_4$-alkylsilyl protecting group.

5. The compound according to claim 1 wherein R is selected from the group consisting of tetrahydropyran-2-yl, 2-methoxyprop-2-yl, trimethylsilyl and triethylsilyl.

6. The compound according to claim 1 which is 9-(2-Furyl)-9-(tetrahydropyran-2-yloxy)-2-methylsulfinyl-2-methylthiononan-1-ol.

7. The compound according to claim 1 which is 9-(2-Furyl)-9-(2-methoxyprop-2-yloxy)-2-methylsulfinyl-2-methylthiononan-1-ol.

8. The compound according to claim 1 which is 9-(2-Furyl)-9-trimethylsiloxy-2-methylsulfinyl-2-methylthiononan-1-ol.

9. The compound according to claim 1 which is 8-(2-Furyl)-8-(tetrahydropyran-2-yloxy)-2-methylsulfinyl-2-methylthiooctan-1-ol.

10. The compound according to claim 1 which is 10-(2-Furyl)-10-(tetrahydropyran-2-yloxy)-2-methylsulfinyl-2-methylthiodecan-1-ol.

* * * * *